US009649249B1

(12) United States Patent
Green

(10) Patent No.: US 9,649,249 B1
(45) Date of Patent: May 16, 2017

(54) PENILE PROSTHETIC SYSTEM

(71) Applicant: Gerald Scott Green, Ellicott City, MD (US)

(72) Inventor: Gerald Scott Green, Ellicott City, MD (US)

( * ) Notice: Subject to any disclaimer, the term of this patent is extended or adjusted under 35 U.S.C. 154(b) by 0 days.

(21) Appl. No.: 15/080,851

(22) Filed: Mar. 25, 2016

Related U.S. Application Data

(60) Provisional application No. 62/177,798, filed on Mar. 25, 2015.

(51) Int. Cl.
*A61H 19/00* (2006.01)
*A61F 2/50* (2006.01)

(52) U.S. Cl.
CPC .............. *A61H 19/44* (2013.01); *A61F 2/50* (2013.01)

(58) Field of Classification Search
CPC ...... A61F 5/40; A61F 7/10; A61F 7/00; A61F 2007/105; A61F 2007/0048
USPC ..................................................... 600/38–41
See application file for complete search history.

(56) References Cited

U.S. PATENT DOCUMENTS

| | | | |
|---|---|---|---|
| 3,809,090 A * | 5/1974 | Povlacs ..................... A61F 6/04 | 604/347 |
| 5,014,446 A * | 5/1991 | Reesman ................. F26B 9/003 | 34/197 |
| 5,823,939 A * | 10/1998 | Tsagarakis ................ A61F 5/41 | 600/38 |
| 5,842,970 A | 12/1998 | Lakusiewicz | |
| 6,547,717 B1 * | 4/2003 | Green ........................ A61F 5/41 | 600/38 |
| 6,599,236 B1 * | 7/2003 | Castro .................... A61H 19/44 | 600/38 |
| 6,776,755 B1 | 8/2004 | Raskin | |
| 7,214,204 B2 * | 5/2007 | Nan ........................ A61H 19/44 | 601/46 |
| 7,261,685 B2 | 8/2007 | Wu | |
| 7,871,386 B2 | 1/2011 | Nan | |
| 8,545,392 B2 | 10/2013 | Standfest et al. | |
| 8,764,629 B2 | 7/2014 | Braud | |
| 8,974,369 B2 | 3/2015 | Tomlinson, Jr. | |
| 2003/0236444 A1 | 12/2003 | Brown, Jr. | |
| 2008/0082028 A1 | 4/2008 | Blevins | |
| 2008/0108863 A1 | 5/2008 | Stephenson | |
| 2009/0005714 A1 | 1/2009 | Mecenero | |
| 2009/0131744 A1 | 5/2009 | Pattenden | |
| 2009/0275796 A1 | 11/2009 | Gil | |
| 2010/0204542 A1 | 8/2010 | Hodge | |
| 2014/0135574 A1 | 5/2014 | Gannam | |

(Continued)

*Primary Examiner* — Samuel Gilbert
(74) *Attorney, Agent, or Firm* — Rosenberg, Klein & Lee

(57) ABSTRACT

A thermally regulated penile prosthetic system includes a prosthetic capsule extending longitudinally from a base to define a shaft region terminating at a tip region. The prosthetic capsule includes an inner capsule portion nested within an outer capsule portion and a fluid cushion captured therebetween. The inner capsule portion defines an inner bore extending from the base region longitudinally through the shaft region, the inner capsule portion being supported with respect to the outer capsule portion at the tip region by a stabilizing member. A heating source is coupled to transfer heat to the prosthetic capsule; and, an outer skin layer extends substantially about at least a portion of the shaft region of the prosthetic capsule. The outer skin layer is configured to emulate penile shaft skin.

20 Claims, 6 Drawing Sheets

(56) References Cited

U.S. PATENT DOCUMENTS

| | | |
|---|---|---|
| 2014/0171734 A1 | 6/2014 | Kassman |
| 2014/0296627 A1 | 10/2014 | Forsell |
| 2015/0119636 A1* | 4/2015 | Yenko .................... A61H 19/34 600/38 |
| 2015/0141748 A1 | 5/2015 | Campbell |
| 2015/0157531 A1 | 6/2015 | Sedic |
| 2015/0182371 A1 | 7/2015 | Owens |
| 2015/0290022 A1 | 10/2015 | Crosby |

* cited by examiner

PENILE PROSTHETIC SYSTEM

BACKGROUND OF THE INVENTION

The present invention is generally directed to a system providing an externally donned penile prosthetic device for those struggling to develop or maintain sufficient erection for sexual intercourse. More specifically, the present invention is directed to a system providing such penile prosthetic device equipped with measures for enhanced lifelike replication of a naturally erect penis. During use, the penile prosthetic device takes on much the overall shape, degree of firmness, and warmth of a naturally erect penis, so as to optimize the pleasure and normal physiological response of a user's sexual partner.

Currently, numerous factors such as erectile dysfunction (ED), general fatigue, physiological changes due to aging, psychological/physiological irregularity, and the like are known to impair men's ability to achieve and maintain sufficient penile erection to engage in sexual intercourse. Many men suffer to different degrees from these or other conditions, and are unable to engage in normal sexual relations without the aid of pharmaceutical or other more invasive medical intervention. Even with significant intervention, beneficial results are often not accessible in timely manner, or simply are not consistently reliable. This leads to sexual dissatisfaction, and loss of men's confidence in the inability to satisfy their mates. This in turn leads to further cycles of sexual dysfunction, consequent dissatisfaction and loss of confidence, and so on.

There are various conventional options available to those suffering from ED or other such conditions leading to impaired erection. They include remedial devices, such as vacuum pumps that increase blood flow to the penis; medications such as ingested pills or direct injections into the penis; or, even surgery to place penile implants, for instance. Certain other available options include psychological evaluations, herbal remedies, testosterone treatments, and the like. Still other options include extraneous sexual accessories or implements, like so-called sex toys. Again, these available options suffer in varying degrees from such drawbacks as undue invasiveness, limited accessibility, and unreliable effectiveness.

There is therefore a need for a system which provides minimally invasive and readily accessible measures which enable convenient use, comfort, and satisfaction for both the user and his sexual partner.

SUMMARY OF THE INVENTION

It is an object of the present invention to provide a system that enables a user to simply and conveniently achieve apparent penile erection to engage in sexual intercourse.

It is another object of the present invention to provide a system having an externally worn penile prosthetic device that emulates the shape and feel of a natural erect penis.

It is yet another object of the present invention to provide a system whose main components are reusable and easily maintained between uses.

These and other objects are attained in a penile prosthetic system comprising a prosthetic capsule extending longitudinally from a base to define a shaft region terminating at a tip region. The prosthetic capsule includes an inner capsule portion nested within an outer capsule portion and a fluid cushion captured therebetween. The inner capsule portion defines an inner bore extending from the base region longitudinally through the shaft region, the inner capsule portion being supported with respect to the outer capsule portion at the tip region by a stabilizing member. An outer skin layer extends substantially about at least a portion of the shaft region of the prosthetic capsule. The outer skin layer is configured to emulate penile shaft skin.

Preferably, in certain embodiments, a heating source is coupled to the prosthetic capsule. The heating source is suitably configured to transfer heat to the prosthetic capsule for thermal emulation of a naturally erect penis.

In certain embodiments, a penile prosthetic system is provided which comprises a pelvic base having a substantially planar body and a base opening formed therethrough. A prosthetic capsule having a base region detachably is coupled to the pelvic base, the prosthetic capsule extending longitudinally from the base region to define a shaft region terminating at a tip region. The prosthetic capsule includes an inner capsule portion nested within an outer capsule portion and a fluid cushion captured therebetween. The inner capsule portion defines an inner bore extending from the base region longitudinally through the shaft region, with the inner capsule portion being supported with respect to the outer capsule portion at the tip region by a stabilizing member. The inner capsule portion is supported at the base region with the inner bore thereof aligned in open communication with the base opening of said pelvic base. A heating source is coupled to the inner capsule portion to transfer heat thereto. An outer skin layer is provided to extend substantially about at least a portion of the shaft region of the prosthetic capsule, the outer skin layer being configured to emulate penile shaft skin.

In certain other embodiments, a penile prosthetic system having thermal regulation is provided, comprising a pelvic base having a substantially planar body and a base opening formed therethrough. The pelvic base includes at least one retention strap coupled to the planar body for adjustable securement about a portion of a user's body. A prosthetic capsule having a base region is detachably coupled to the pelvic base, which prosthetic capsule extends longitudinally from the base region to define a shaft region terminating at a tip region. The prosthetic capsule includes an inner capsule portion nested within an outer capsule portion and a fluid cushion sealed within a canal defined therebetween. The inner capsule portion defines an inner bore extending from the base region longitudinally through the shaft region, and is supported with respect to the outer capsule portion at the tip region by a stabilizing member projecting to matingly engage a tip passage formed through the outer capsule portion at the tip region. The stabilizing member defines a transfer tube for open communication therethrough between the inner bore and tip passage of the inner and outer capsule portions. The inner capsule portion is supported at the base region with the inner bore thereof aligned in open communication with the base opening of the pelvic base. Each of the inner and outer capsule portions is formed of a resilient material, with the inner capsule portion being configured with greater firmness than the outer capsule portion. At least one helical heating element is integrated in the inner capsule portion to extend about an outer wall of said inner capsule portion substantially through the shaft region. The helical heating element being thermally charged responsive to actuation through a link to an external source passed through the prosthetic capsule and the pelvic base. An outer skin layer is provided to extend substantially about at least a portion of the shaft region of the prosthetic capsule, the outer skin layer being configured to emulate penile shaft skin.

DETAILED DESCRIPTION OF THE PREFERRED EMBODIMENTS

Briefly, the subject system provides generally for a penile prosthetic device that may be quickly and conveniently worn by a user to make ready for sexual intercourse with his partner, even if he is unable to achieve natural penile erection at that time. The user dons the prosthetic device over his own penis, preferably with the prosthetic device retentively secured at or near its base to a pelvic base portion that is held firmly to the user's groin area. The pelvic base portion is then also worn by the user, with suitable retention measures to hold such pelvic base portion securely yet comfortably in place.

The prosthetic device is preferably formed with multiple layers of materials of graduated firmness. The outermost layer(s) which makes direct contact with the sexual partner is formed of the softest, least firm resilient material of the layers to effectively reproduce the softness and perhaps even the elasticity of natural skin tissue at the tip and around the shaft of a natural penis. The erect form of the prosthetic device is supported by one or more inner layers formed preferably though not necessarily of resilient material of suitable firmness to maintain the degree of rigidity typical of a healthy man's naturally erect penis. Preferably, a fluid component is intermediately captured between two or more layers of the device to further graduate the balance of softness and rigidity characteristic of a naturally erect penis (in addition to provide other advantages, such as to effect even thermal distribution throughout the device).

The prosthetic device is thus suitably shaped, sized, and formed of such material composition to suitably replicate the natural coital form of the user's penis. The prosthetic device is suitably formed to replicate also the natural feel of the user's erect penis for the user's sexual partner. Toward that end, the system preferably includes one or more heating sources which serve to thermally regulate the prosthetic device. The heating source may be of any suitable type known in the art, including either passive or active measures for heat transfer to the prosthetic device.

As implemented in certain exemplary embodiments, the subject system thus provides for an externally donned penile prosthetic device for those struggling to develop or maintain sufficient erection for sexual intercourse. The penile prosthetic device is equipped with measures for enhanced lifelike replication of a naturally erect penis, preferably including its thermal properties. During use, the penile prosthetic device thereby takes on much the overall shape, degree of firmness, and warmth of a naturally erect penis, so as to optimize the pleasure and normal physiological response of the user's sexual partner.

Figure 1:
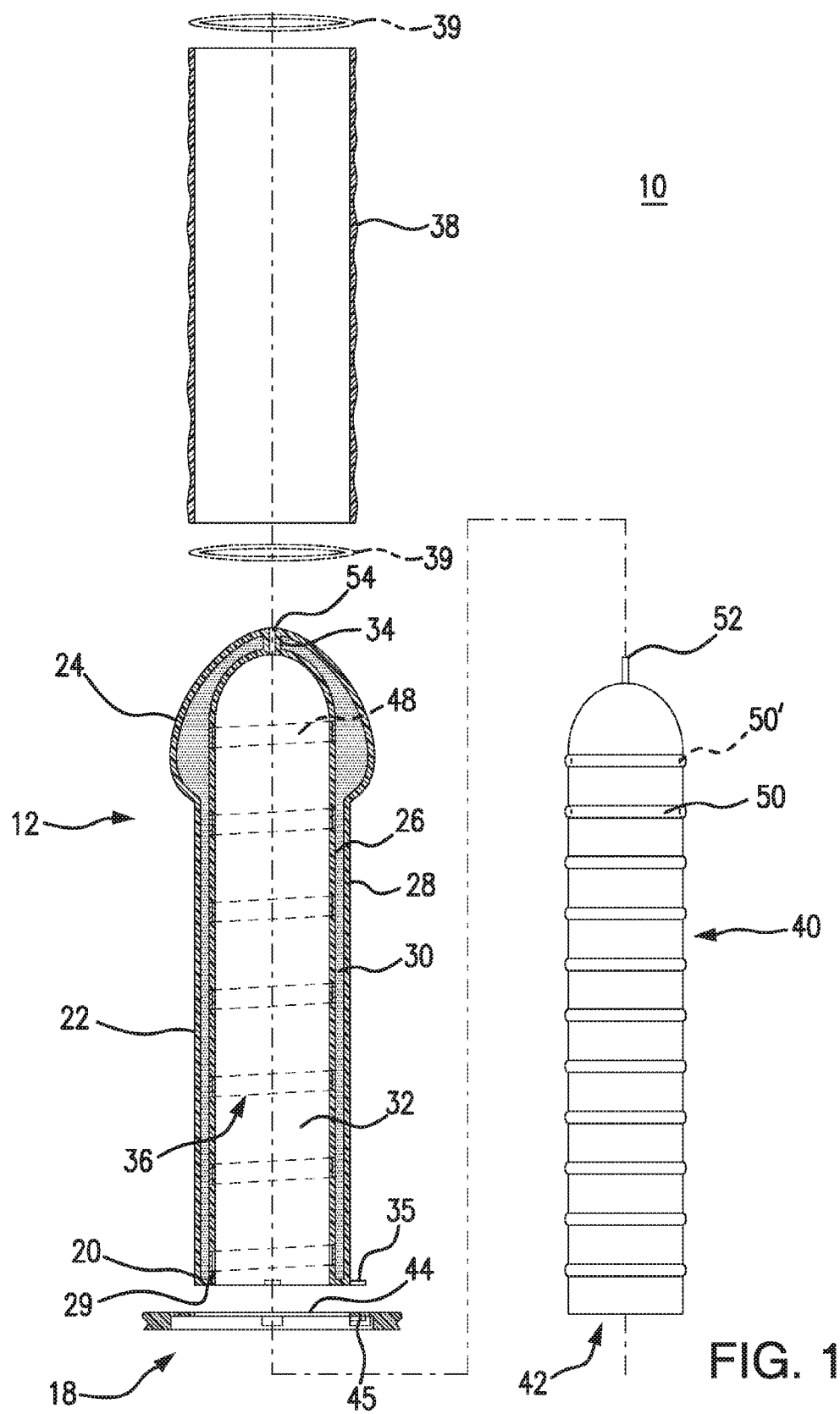
FIG. 1 is an exploded plan view, partially cut away, of a prosthetic device and pelvic base formed in accordance with one exemplary embodiment of the present invention, schematically illustrating the intercoupling of certain portions.

Referring now to FIG. 1, there is illustrated certain portions of a penile prosthetic system 10 formed in accordance with one exemplary embodiment of the present invention. In these and other figures, the various portions of the system are illustrated with shapes, contours, and/or relative dimensions which are simplified (and even exaggerated) in the interests of clarity and brevity of description. Those skilled in the art will readily recognize that the portions of the system disclosed and described herein may be variously shaped, contoured, and relatively sized to suit the particular requirements and/or particular user preferences in a given application.

The thermally regulated penile prosthetic system embodiment 10 illustrated herein is but one of numerous configurations with which the subject system may be realized in accordance with the present invention. System 10 includes a prosthetic capsule 12 worn over the user's penis as needed, to address the ill effects of erectile dysfunction and other issues that typically undermine sexual performance and lead to sexual dissatisfaction. The prosthetic capsule 12 is configured to substantially replicate the user's erect penis in its natural form and appearance, as well as its natural bodily heat. The prosthetic capsule 12 is preferably tailored in size and shape for suitable fit over the user's naturally-erect penis received within it during use. Its inner bore is preferably configured to receive even the user's non-erect penis in substantially conformed manner for comfortably stable fit, yet provide ample resilience and room to accommodate full or partial erection during use without compromising such comfort and stable fit.

Preferably, the appearance of the prosthetic capsule 12—its visible surface contours and colors are matched accordingly to closely mirror the user's penis. The physical properties of the prosthetic capsule 12 are such that the capsule provides for the sexual partner a sensation similar to that of the user's naturally-erect penis. The prosthetic capsule 12 effectively replicates the shape, size, color, and feel of the user's penis when it is erect. It provides spontaneous and improvisatory sexual satisfaction to the user's partner notwithstanding the user's inability to attain a natural erection.

Since it is externally worn, the length and girth of the prosthetic capsule 12 is slightly larger, preferably, than that of the user's natural penis to so accommodate its expansion within, and easy withdrawal from, the capsule. Alternative measures are provided in the prosthetic capsule 12 for either ejection or retention of bodily fluid within/from the prosthetic capsule 12. The close lifelike appearance of the prosthetic capsule 12 coupled with its palpable feel (similar to that of the user's penis) make for a viable option to those struggling with penile erection.

The prosthetic capsule's stable fit is reinforced by its securement to a pelvic base 18, which in turn is secured to the user's body by a retention garment 14. The prosthetic capsule 12 is preferably coupled detachably to the pelvic base 18, and the retention garment 14 preferably includes one or more retention straps by which the user may adjustable secure the prosthetic capsule and pelvic base assembly to his waist, buttocks, and/or thighs for use. The retention garment 14 allows the prosthetic capsule 12 to be held firmly yet adjustably in place so that the capsule may move synchronously with the user's pelvis during use. In certain embodiments, the retention garment 14 provides a platform for holding such portions of the system as a power source (for example, one or more batteries) for a heating source that the capsule may be equipped with.

In certain embodiments, the penile prosthetic system 10 includes a conditioning station 16, which includes a housing structure that preferably defines a carrying case 72. In these embodiments, conditioning station 16 is equipped with one or more hanging members and/or supporting brackets, as well as suitable drying measures for cleaning/drying and safe storage of the prosthetic capsule's various portions.

With specific reference to FIG. 1, the prosthetic capsule 12 generally defines a shaft region 22 extending longitudinally from a base region 20 to a tip region 24. The prosthetic capsule 12 in this embodiment is formed with an inner capsule portion 26 that is coaxially disposed to be nested within an outer capsule portion 28. A fluid cushion 30 is captured within a canal defined between the inner 26 and outer 28 capsule portions. The outer capsule portion 28 is preferably formed of a resilient material such as silicone, rubber, foam, or any other suitable material known in the art which provides a degree of flexibility and resilient give approaching that of natural skin tissue. The inner capsule portion 26 is formed a firmer material than the outer capsule portion 28. It too may be formed of a suitable resilient material, but may also be formed of a suitably known non-resilient material as it is externally buffered by both the outer capsule portion 28 and fluid cushion 30. The inner capsule portion 26 provides the structural support for maintaining the degree of structural rigidity for the capsule 12 approaching that of a man's naturally erect penis.

The base 20, shaft 22, and tip 24 regions of the prosthetic capsule 12 substantially match corresponding regions on a man's naturally erect penis. The user's penis is received within a bore 32 formed inside the inner capsule portion 26. The inner capsule portion 26 then provides the erect structural core protectively covered by the softer, more pliant outer capsule portion 28 and fluid cushion 30. As noted in preceding paragraphs, preferably both the inner 26 and outer 28 capsule portions are made from resilient materials, though the inner capsule portion 26 is configured with greater firmness than the outer capsule portion 28. Firmness may be varied using any suitable measures known in the art. For instance, the different portions may be varied in material composition, or otherwise configured to exhibit different mechanical properties by suitably varying thickness, shape, or other such parameters.

The penile prosthetic system 10 also includes an outer skin layer 38 extends substantially about at least a portion of the prosthetic capsule's shaft region 22. This outer skin layer 38 is configured to emulate penile shaft skin. The layer 38 is formed of a resilient material, such as silicone, rubber, or the like, exhibiting sufficient flexibility and pliability to provide the look and feel of the stretchable and soft skin tissue about the shaft of a man's erect penis. In certain embodiments, the outer skin layer 38 is formed as a stretchable tubular member (preferably, a life-like elastic membrane having color similar to that of the user's skin) which encircles the outer capsule portion 28 intermediately about its shaft region 22. Formed as a separate member, the outer skin layer 38 stretches and flexes in place as permitted by its material makeup, to emulate the stretching movement of natural shaft skin about an erect penile during sexual intercourse. In other embodiments, the outer skin layer is adhered, or otherwise fused, to the outer surface of the outer capsule portion's shaft region 22, to so stretch and flex without the threat of dislodging from the outer capsule portion or excessive displacement from the shaft region thereof.

Placement of the penile shaft skin-emulating outer skin layer 38 about the prosthetic capsule's shaft region 22 enhances the life-like appearance of the prosthetic penile capsule 12. Where the outer skin layer 38 is configured as a separate, removable tubular membrane, the outer skin layer 38 may be configured as one of numerous disposable components (formed for example from latex, polyurethane, or other such material having suitable elasticity) offering different selectable appearance and material properties to suit the intended use. The disposable outer skin layer may be formed for instance to be transparent/opaque, colored or non-colored as desired. In these embodiments, each end of the disposable outer skin 38 is preferably secured by a stretchable ring (of rubber or other such material to provide variable diameter) configured to engage respective notches, annular slots, or the like formed accordingly into the outer surface of the outer capsule portion 28 at/near the proximal and distal ends of its shaft region 22. If necessary for a particular application, a removably configured outer skin layer 38 may be secured in place by one or more elastic O-ring members 39 (placed for instance about opposed ends of the outer skin layer 38 within the shaft region 22 but near the base and tip regions 20, 24) stretched thereabout for suitably constrictive grip.

With further reference to FIG. 1, the fluid cushion 30 between the inner and outer capsule portions 26, 28 of the prosthetic capsule 12 provides the user's partner with a buffer against direct contact with the relatively rigid inner capsule portion 26. This fluid cushion 30 is preferably of gel, liquid, gaseous, or any other suitable form within a sealed canal between the capsule portions 26, 28. The fluid cushion 30 provides a suitable degree of pliant, forgiving flex between the inner 26 and outer 28 capsule portions to enhance the feel of natural, fluid-containing feel of bodily tissue. The fluid cushion 30 also allows for a degree of relative movement between the outer and inner capsule portions 28, 26, further enhancing the feel of natural skin tissue about internally supporting muscular or other structure.

Additionally, the fluid cushion 30 and the insular canal that it fills serve to both distribute and store heat transferred from the heat source elements 48 coupled to the inner capsule portion 26 in the illustrated embodiment. This heat, which replicates the user's natural body heat, adds to the palpable and life-like feel provided by the prosthetic capsule 12. In certain embodiments, the fluid cushion 30 fills a canal space having, for example, approximately ½ inch space extending to form a dome-shaped chamber between the nested inner and outer capsule portions 26, 28.

Figure 2:
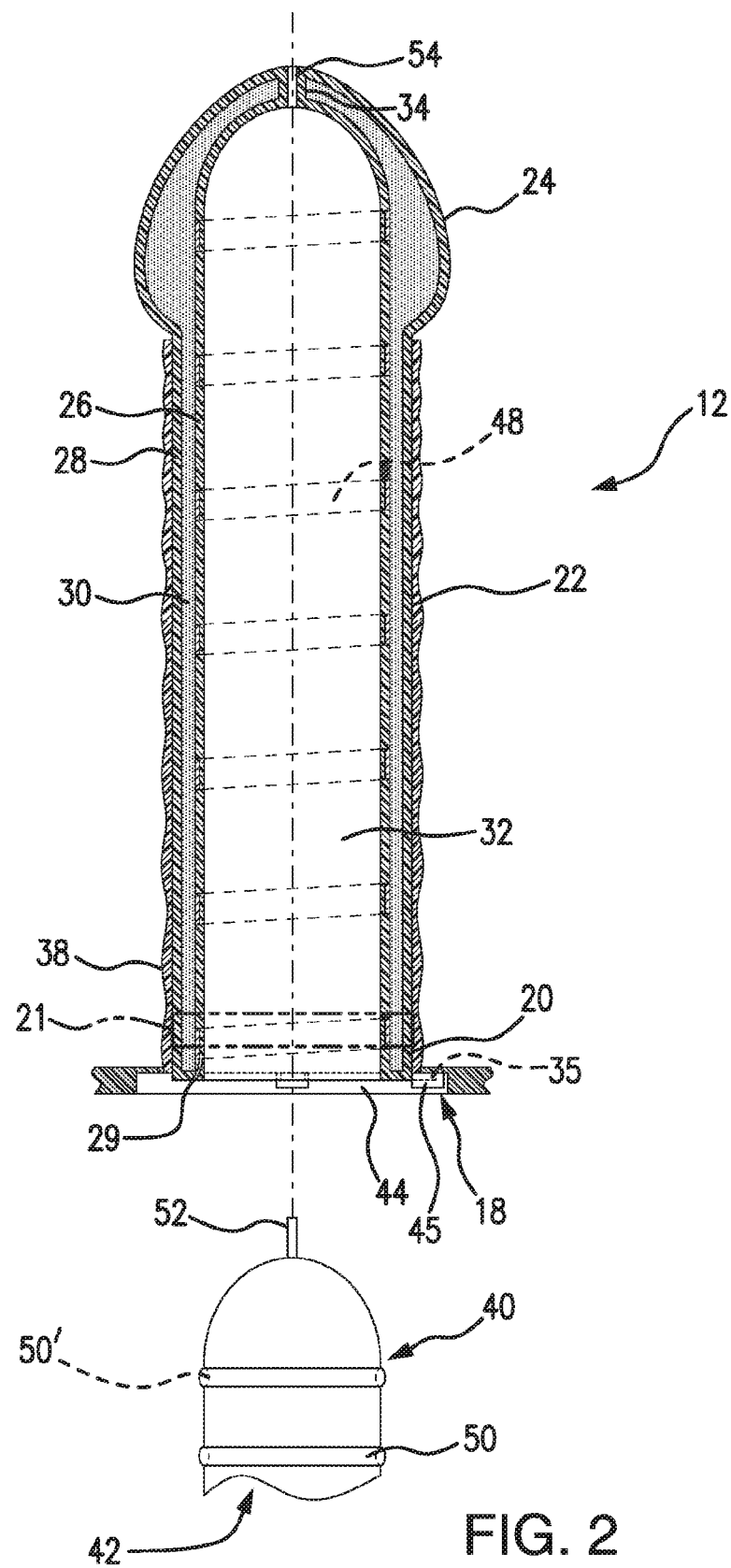
FIG. 2 is a partially exploded plan view, partially cut away, of the prosthetic device of FIG. 1.

With reference to FIG. 2, the inner capsule portion 26 is formed accordingly to accommodate the user's penis, and extend substantially into the outer capsule portion to provide the prosthetic capsule 12 with sufficient firmness and stability for effective coital penetration during sexual intercourse. The inner capsule portion 26 defines an inner bore 32 which extends from the base region 20 longitudinally through the shaft region 22. The user's penis is received in this inner bore 32. The inner bore 32 is structured to allow enough room for the user's penis to expand and contract therein, allowing the penis to remain comfortably positioned therein whether it stays limp or achieves some degree of erection during use. The inner and outer capsule portions 26, 28 are secured to one another preferably at the base region 20.

The inner capsule portion 26 is also supported with respect to the outer capsule portion 28 preferably at or near the apex of the tip region 24 by a stabilizing tube member 34. This tube member 34 spans the canal space between the inner and outer capsule portions 26, 28 there, and preferably opens communication between the inner bore 32 and external space beyond the tip region 24. The length of the stabilizing member 34 from the distal tip of the inner capsule portion 26 to the head of the outer capsule portion 28 is determined according to the requirements of the intended application and/or user preference. In certain embodiments, the stabilizing member 34 may be formed with a solid or otherwise internally closed configuration such that it provides stabilization between the inner and outer capsule portions 26, 28 at the tip region 24 without necessarily providing open access to the inner bore 32 therethrough. In certain other embodiments, the stabilizing member 34 projects from the inner capsule portion 26 to matingly engage a tip passage 54 formed through the outer capsule portion 28 (at the tip region 24). In these embodiments too, a transfer tube defined by the stabilizing member 34 allows open communication through such transfer tube between the inner bore 32 and the tip passage 54.

In certain embodiments, a capsule liner 40 is provided which may be removably inserted within the inner capsule portion's inner bore 32. The capsule liner 40 is formed preferably of a rubber, latex, plastic, or other such elastic material known in the art. The capsule liner 40 is configured to define an inner space 42 to receive the user's penis in substantially conformed manner. Acting much like a condom, the capsule liner 40 provides a protective, preferably disposable, layer of protection for the user's penis and aids its comfortable positioning within the prosthetic capsule 12.

In order to enhance the user's own sexual experience, and even promote natural erection during use, the capsule liner 40 is formed with a plurality of annular (or helical) ribs 50 protruding radially inward (as indicated by the hidden portions 50') into the inner space 42. The inward protrusions 50' of the ribs 50 bear against to maintain arousing contact on the user's penis during use, thereby heightening stimulation towards and possibly urging erection. The ribs 50 may also protrude radially outward (though they may not in certain embodiments) to enhance gripping engagement of the inner capsule portion's surrounding wall surface about the inner bore 32. This helps to more securely keep the inner capsule portion 26 fitted over the user's penis during sexual activity.

In the illustrated embodiment, the capsule liner 40 converges to a liner tip 52 positioned to substantially align with the stabilizing tube member 34 when the capsule liner 40 (having received the user's penis) is inserted into the inner bore 32. In those exemplary uses where the user desires that bodily fluid be conveyed outside the prosthetic capsule 12, the liner tip 52 is opened. An open stabilizing tube member 34 then guides fluid released through the liner tip 52 out through the tip of the outer capsule portion 28. Sufficient alignment between the stabilizing member 34 and the liner tip 52 ensures that the fluid is not scattered inside the capsule liner 40 or the inner bore 32, but ejected from the prosthetic capsule 12 in concentrated manner. Where, on the other hand, bodily fluid is to be contained and not ejected through the prosthetic capsule 12, the liner tip 52 may be closed off so that any bodily fluid released within the capsule liner 40 remains trapped therein.

With further reference to FIGS. 1-2, the prosthetic capsule 12 is provided with a heating source 36 coupled thereto. In order to fully replicate the user's sexual experience with their partner, the bodily heat produced by the user's penis is reproduced for the prosthetic capsule 12 in this manner. The heating source 36 may be realized in a wide variety of forms. It may be thermally charged by various passive or active measures known in the art. For example, the heating source 36 may include a ceramic or other element passively charged by thermal contact with a heated medium then placed in contact with the prosthetic capsule 12. The heating source 36 may otherwise include active electrical, chemical, or even mechanical measures for generating the required heat. In the illustrated embodiment, for instance, the heating source 36 includes one or more electrically driven heating elements 48 embedded on the inner capsule portion 26 to extend helically thereabout.

This heating element 48 so disposed on the inner capsule portion 26 extends about and along an outer wall surface of that inner capsule portion 26, substantially through the shaft region 22. The heating element 48 is preferably exposed to the canal defined between the inner and outer capsule portions 26, 28 for contact (or communication) with the fluid material forming the fluid cushion 30. Heat generated or otherwise supplied by the heating element 48 is transferred to the fluid making up the cushion 30 for efficient, even distribution throughout the canal and consequently evenly distributed transfer to the outer capsule portion 28. The heat thus transferred to the outer capsule portion 28 is then transferred both by contact and radiation to the user's sexual partner, thereby emulating the natural warmth of the user's penis.

In certain embodiments, such thermal control and regulation over the fluid making up the cushion 30 may provide other benefits. Depending on the material composition of fluid cushion 30, variation in the heat provided by the heating element 48 may vary the fluid's properties enough for functional modulation or tuning of prosthetic device's properties. For example, thermal control of the fluid may vary its viscosity to make for fine tuning of the device's overall stiffness, with for instance thicker viscosity tending to heighten stiffness of feel and thinner viscosity tending to lessen stiffness of feel.

Any suitable switching or control measures known in the art may be employed in this regard. Such control measures (not shown) would be operably coupled through hardwired or wireless measures to the heating source and/or its power source to effect the required tuning/modulation control. Pulsed or otherwise modulated tuning of the fluid cushion's thermal properties may be used to accentuate stimulating sensations and/or natural lifelike pulsations produced by the prosthetic device.

The heating element 48 is energized through one or more electrical conductors guided through respective openings formed through the inner and/or outer capsule portions 26, 28 and pelvic base 18. The heating element 48 may be disposed in a variety of patterns other than the helical/spiral pattern shown. The heating element 48 may be connected through wires or other equivalent conductive measures known in the art to a power source located either on the prosthetic capsule 12 itself or located external to such prosthetic capsule. In an embodiment where the power source includes one or more batteries held on the retention garment 14, wires connecting the power source with the helical heating element 48 may be suitably routed via one or more through ports 29 formed in the intervening components/portions (such as indicated in FIGS. 1 and 2). Energizing the power source excites the heating element 48 to, for instance, resistively heat the fluid cushion 30 (and inner capsule portion 26). This heat is then transferred by the fluid cushion 30 which distributes the heat for further even transfer to the outer capsule portion 28 and outer skin layer 38. The tip and head regions of the prosthetic capsule 12 are then evenly heated to replicate the body-like heat of the user's naturally erect penis.

In an alternate embodiment, the heating source 36 may use thermal convection to heat the prosthetic capsule 12. For example, a heating element may be disposed on the inner capsule portion 26 to extend thereabout. Just prior to using the prosthetic capsule 12, the user may place the capsule in an oven-like compartment, or in thermally conductive contact with an external heat source. After a certain heating period of time has elapsed, the user may remove the heated prosthetic capsule 12 for use, the capsule 12 substantially retaining the heat for the duration of use to replicate natural body heat. Among the advantages of such embodiment are the elimination of accompanying power sources like batteries and elaborate routing of wires and the like. This results generally in a simpler and less cumbersome-to-use penile prosthetic system 10.

In certain exemplary applications and embodiments, the prosthetic capsule 12 may be selectively bendable to a certain degree. In these embodiments, an optional bend junction 21 is defined at or near the capsule's base region 20 allowing the prosthetic capsule 12 to bend in angular orientation relative to the base 20. The optional bend junction may be realized by a zone configured on the inner and outer capsule portions 26, 28 to permit sufficient flex for bending. Corresponding zones may be formed using any suitable measures known in the art, such as by thinning the walls of the capsule portions within the zones, forming a joint between wall segments, by interposing an intermediate section to provide suitable flex, or the like. The sexual experience is enhanced for both the user and partner by the accommodated bending of the prosthetic capsule 12, which serves to better enable the natural bending response of the user's actual penis during intercourse. In certain embodiments, the optional bend junction may be positioned, for example, approximately 1/16 inch ahead (longitudinally) of the retention garment 14 to allow the prosthetic capsule 12 to bend to the desired angle. In certain embodiments, the bend junction 21 may include a strong yet malleable member disposed in or on the inner and outer capsule portions 26, 28 to allow also for user adjustment in the angle by which the prosthetic capsule 12 generally emerges from its base region 20 and/or the pelvic base 18.

Referring to FIGS. 1-2 and 5-6, in the illustrated embodiment, the penile prosthetic system 10 includes a pelvic base 18 having a base opening 44 formed therethrough. Depending on the preference of the user, the shape of this pelvic base 18 may be tailored to comfortably fit the user's groin area. In the illustrated embodiment, the pelvic base 18 is formed as a shield-like body providing a substantially planar support surface. Moreover, the prosthetic capsule 12 is detachably coupled to the pelvic base 18 at its base region 20. When the prosthetic capsule 12 is properly positioned, its base region 20 is supported by the pelvic base 18 with its inner bore 32 aligned in open communication with the base opening 44 of the pelvic base 18. This detachable coupling between the pelvic base 18 and the prosthetic capsule 12 allows for this prosthetic capsule to be effortlessly received around the pelvic area of the user.

The prosthetic capsule 12 may be retentively yet detachably fastened to the pelvic base 18 through locking tabs 35 and matching sockets 45, clipping brackets (see FIG. 4), or other such retaining structures mated thereto. Mated pairs of locking tabs and retaining structures positioned on respective ones of the capsule's base region 20 and the pelvic base 18 interlock with one other when the prosthetic capsule 12 is assembled with the pelvic base 18. Each of the locking tabs and corresponding socket structures may be formed on either one of the intercoupled portions, so long as appropriately mated pairs of tab/retaining structures are disposed to oppose one another. An added benefit of the pelvic base 18 is the protection it affords—allowing the capsule to find adequate rest and support at its base region without exerting too much direct force on the pelvic area of the user. This mitigation of the direct force applied on the pelvic area of the user preserves a pleasurable sexual experience for the user.

Figure 6:
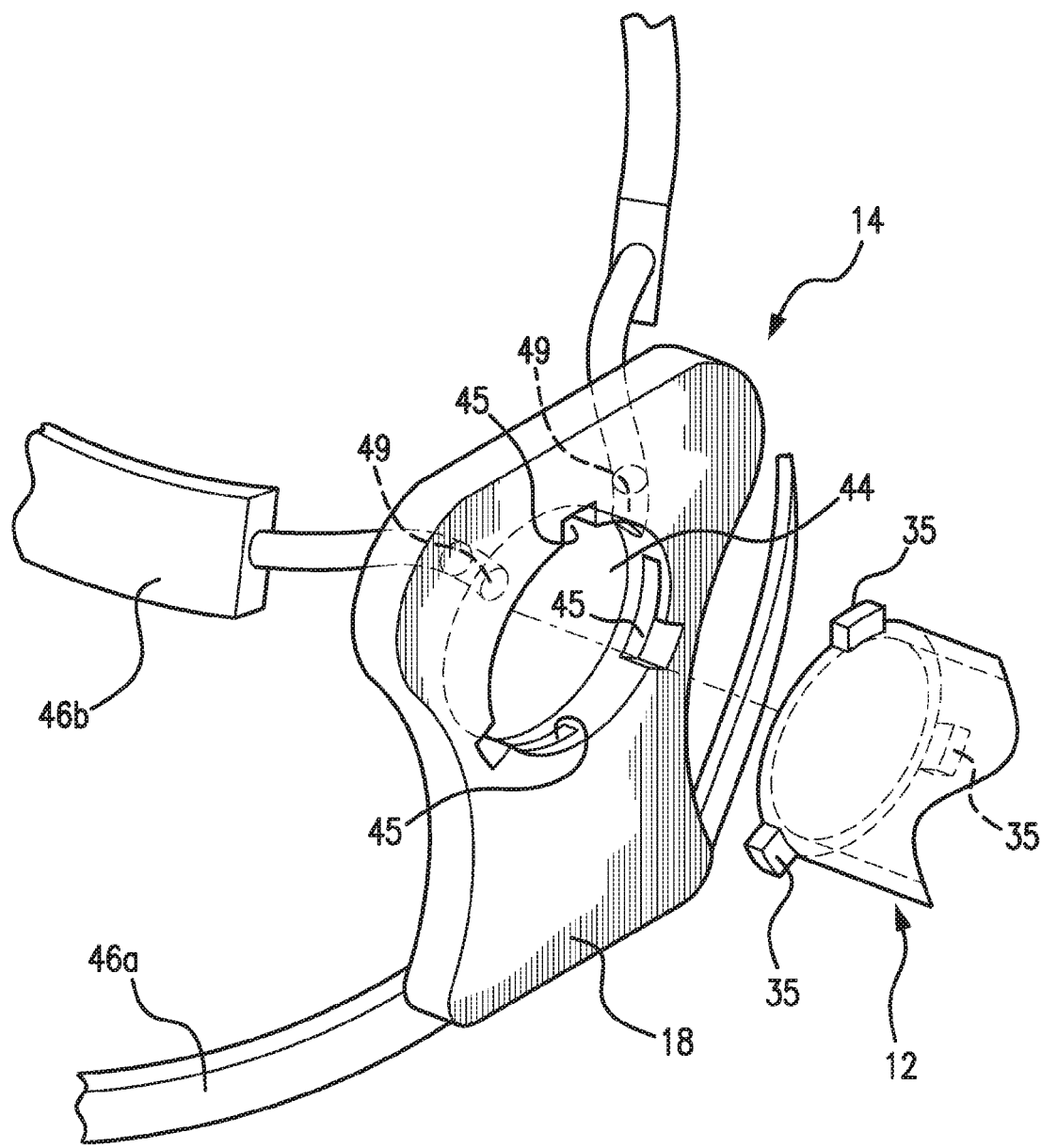

As shown in FIG. 6, the socket structures 45 are formed into the pelvic base 18 in the illustrated embodiment. Each socket structure 45 defines a slot cut into the pelvic base material, which slot communicates with a recessed area formed in the planar outer surface of the pelvic base 18 about the base opening 44. Thus, when the base end of the socket capsule 12 is inserted in substantially concentric alignment with the base opening 44, it is seated by the tabs 35 first engaging the recessed areas of the socket structures 45, then sliding along an angular path therefrom (upon rotation of the prosthetic capsule 12) into engagement with the slots extending respectively from those recessed areas. Any electrical coupling wires passed through the retention straps (through straps 46b, for instance) are guided by through ports 49 suitably formed in the pelvic base material (to communicate with the opening 44), and from there passed into a correspondingly positioned through port 29 of the prosthetic capsule 12 for coupling to the heating source 36 disposed therein.

Figure 4:
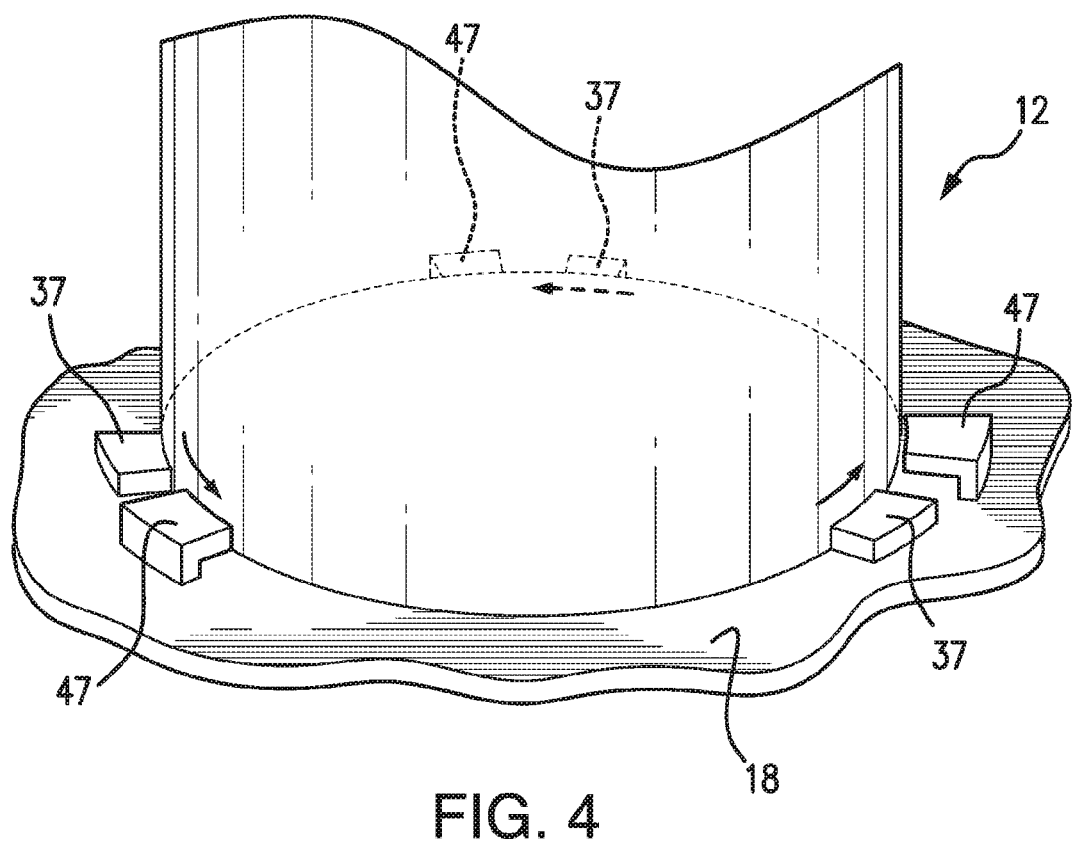
FIG. 4 is an enlarged perspective view of a portion of the prosthetic device and pelvic base of FIG. 1, schematically illustrating one example of releasable retentive coupling operation therebetween.

FIG. 4 illustrates a departure from the tab and socket structure shown in the embodiment of FIGS. 1-2. In this alternate embodiment, the retaining structures for the tabs 37 formed on the prosthetic capsule 12 are formed on/mounted to for instance on the planar surface of the pelvic base 18 as shown. While otherwise similar in structural configuration to the tabs 35 of the preceding embodiment, the tabs 37 in this embodiment are offset accordingly in position from the very end of that base 20 to firmly engage the retaining structures formed as surface mounted clipping brackets 47. The clipping brackets 47 are each preferably formed with wall surfaces overhanging and laterally stopping a slot defined over the pelvic base surface. When a matching tab 37 is angularly displaced (by rotation of the prosthetic capsule 12 upon seating within the pelvic base's opening 44), the tab 37 inserts into the slot until it bears up against the stopping wall at the opposing lateral end of the clipping bracket 47.

Figure 5:
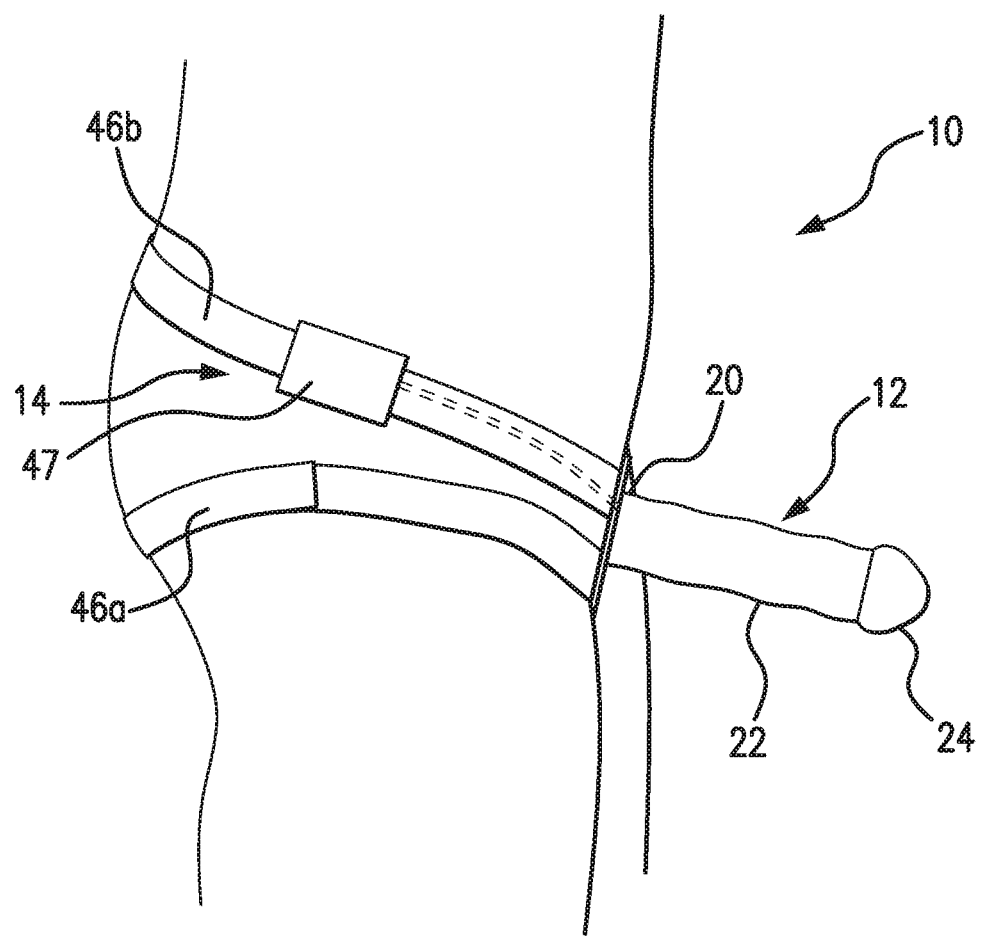
FIG. 5 is an elevational view schematically illustrating the prosthetic device and pelvic base of FIG. 1, as equipped with a retention garment and worn for use by a user; and, FIG. 6 is an enlarged perspective view, partially cut away and exploded, schematically illustrating releasable retentive coupling between the prosthetic device and pelvic base in the embodiment of FIG. 1, with certain portions of a retention garment coupled to the pelvic base.

With particular reference to FIGS. 5-6, the retention garment 14 is coupled in the illustrated embodiment to the pelvic base 18 for adjustable securement about the pelvic portion of the user's body. For example, in certain uses, the retention garment 14 includes one or more thigh retention straps 46a which secure to the pelvic base 18. The retention garment may also include one or more waist/buttock retention straps 46b which firmly secure to the pelvic base 18. Adjustable use of one or more such straps 46a, 46b to adjustably secure the pelvic base 18 to the user, stabilizes support for the prosthetic capsule 12 in place over and about the user's penis. This retention garment 14 serves, among other things, to obviate the need for other more complex or invasive measures for keeping the prosthetic capsule 12 properly in place during use.

The retention garment 14 may also include other features such as a power source storage mechanism and/or control mechanism for the prosthetic capsule 12 stored in a utility unit 47. In certain embodiments, this power storage mechanism may store a battery pack connected by wires to the heating source 36 to provide heat to the prosthetic capsule 12. In such embodiments, low voltages batteries may be stored. For example, a lithium ion battery pack having a certain voltage rating may be equipped with user control measures for selective setting between low, medium, high, or other such settings depending on the amount of heat desired.

Figure 3:
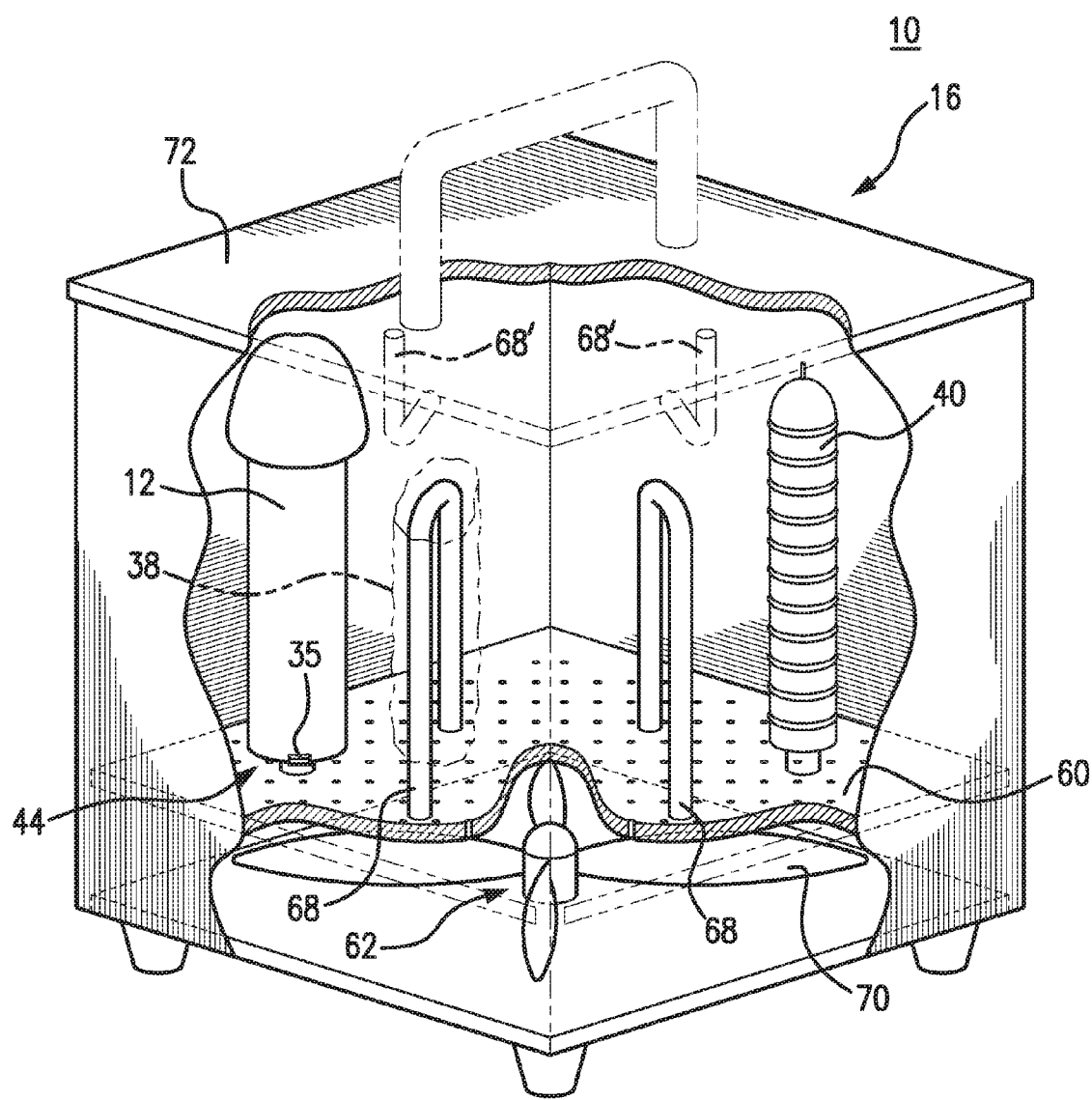
FIG. 3 is a perspective view, partially cut away, of a station for conditioning formed in accordance with another exemplary embodiment of the present invention, illustrating the conditioning storage of certain components of the prosthetic device of FIG. 1.

With specific reference to FIG. 3, in certain embodiments, a thermally regulated penile version of the prosthetic system 10 may include a conditioning station 16 that facilitates convenient and hygienic storage and maintenance of the prosthetic capsule 12. The prosthetic capsule 12 may be cleaned and dried as illustrated within the conditioning station 16. The conditioning station 16 is equipped with a support panel 60 which extends over a blower compartment 62. In certain embodiments, the support panel 60 includes a perforated surface. A supporting member 68 is coupled to the support panel 60 for receiving one or more portions of the prosthetic capsule 12. The conditioning station 16 is equipped with various hanging members and/or supporting brackets 68 suitably configured and positioned within the conditioning station's inner compartment for resting the different system portions for storage, cleaning, and/or drying.

The conditioning station 16 thus adds to the safety and hygienic aspects of the prosthetic system 10. For example, a fan or other such blower unit 70 is disposed in the blower department 62 and accordingly actuated to generate airflow past the supporting members/brackets 68. Preferably, the conditioning station 16 may be easily assembled and disassembled for transport and storage to meet the user's specific requirements. When assembled and closed, the conditioning station 16 may be configured as a carrying case having a convenient handle for ported transport.

Among the practical advantages provided by the penile prosthetic system 10 is that the user need not undergo surgical or other invasive procedures to utilize the prosthetic capsule 12. The prosthetic system 10 provides a mechanism to conveniently clean, sanitize, and store the prosthetic capsule 12 between uses. Nor must the user carry out extensive prepatory procedures to make proper and effective use of the prosthetic capsule 12. A comfortable and hygienic product is thereby provided by system 10 to mitigate troublesome issues related to sexual dissatisfaction.

For an optimally customized penile prosthetic system 10, the prosthetic capsule 12 is preferably configured for a particular individual user, taking into account the following:
The user's erect penis is measured by suitable means to invoke natural erection;
The user's erect penis is dimensionally characterized;
The skin color of the user's penis is acquired; and
The user's waist and thighs are dimensionally characterized.
The prosthetic capsule 12 is configured according to these and/or other such personalized factors.

Implementation Example

One example of implementation for a sample application of the embodiment shown in FIGS. 1-3 and 5-6 described in detail below in paragraphs throughout this section. This sample application is provided merely as an illustrative example; and, while the various aspects of the sample application and certain alternative variations thereof are described with a corresponding sampling of qualitative and even quantitative details, such sample details are provided for purposes of illustration, and not as required limitations. Various other applications, implementations, or embodiments of the system more generally described herein are not limited to such sample details.

A sample system is formed with the following main components: (I) Prosthetic capsule, (II) Retention Garment, (III) Heat and Comfort Package, (IV) Conditioning station, and (V) Carrying Case. Each of these components may include additional sub-components in certain variations, as further described in the following paragraphs.

Prosthetic Capsule:

The externally worn and life-like prosthetic capsule which fits over the user's penis may include any of the following features in an exemplary implementations and uses:

In certain applications, the pelvic base is detachably coupled to the base region of the prosthetic capsule by mated locking tab structures located on both the pelvic base and prosthetic capsule. The locking tabs may be made of plastic, and interlock with each other when the two components are assembled. In certain embodiments, this pelvic base is made of soft silicone with its inside reinforced with nylon mesh to thereby fit comfortably against the pelvic and groin area of the wearer. The pelvic base may also define pass-through holes/ports for guiding heat wires.

In certain applications, instead of being directly coupled to the pelvic base, the retention straps of a retention garment are each coupled to a yoke structure formed for instance by a rigid annular ring of rubber, plastic or other suitable material known in the art, which is fastened by suitable means to the pelvic base, concentrically about the base opening thereof. The pelvic base extends beyond the outer diameter of such yoke-like annular ring of the retention garment by approximately 1 inch above and 1 inch below for ample support. In such applications, the pelvic base preferably tapers inward in peripheral contour such that its mid-section extends beyond the outer diameter of such yoke-like annular ring by approximately ⅝ inch on each side, to define a generally hour glass contour (such as shown in FIG. 6. Such design facilitates firm, non-slip fit of the yoke structure against the user's pelvic area to reduce compression or discomfort around the testicles and inner thighs. In such applications, the diameter of the base opening in the pelvic base is determined by the diameter (girth) of the prosthetic capsule and its inner components. In certain applications, a recessed entry into the pelvic base surface at the base region of the prosthetic capsule (such as illustrated in 6) does not add to this diameter, but rather is approximately a ⅛ inch wide by 1/16 inch deep indentation around the base opening's circumference.

In certain applications, a receptacle and heat wires pick up connect a battery to energize the heating source. If an optional bend junction is used, these heat wires are preferably coiled to allow for stretching accommodation.

In certain applications, a permanent outer skin layer is formed of a life-like silicone membrane toned in color to the user's skin and fused at the base and/or shaft regions of the prosthetic capsule. In certain other applications, the disposable outer skin layer is made of clear latex or polyurethane to resemble a membrane or condom that is open at both ends. In certain sample applications, each such end is secured by an approximately 1/16 inch thick, variable diameter stretch ring. The ring diameter here is determined by the circumference of the outer capsule portion, and each such ring would fit into an approximately 1/8 inch circumference notch or groove formed into the outer surface at proximal and distal ends of the outer capsule portion. In certain applications, such notches/grooves for attaching the disposable outer skin layer to the outer capsule portion are located at the base region thereof. Furthermore, if a retainer ring is formed into the disposable outer skin layer at opposed ends thereof to be used for secure such disposable outer skin layer in place, but the notches/grooves to which they secure do not provide sufficiently secure retention, retention may be augmented by use of one or more extraneous retainer ring(s) (such as illustrated in FIG. 1). Such extraneous retainer ring(s) may be made of rubber or other such stretchable, elastic material having a thickness, for example, of approximately 1/16 of an inch prior to being stretched.

In certain exemplary applications, the outer capsule portion is made of an approximately 3/16 inch thick soft silicone material which includes a head portion of the prosthetic capsule fabricated to match the user's penis color and shape.

In certain applications, the inner capsule portion is made of an approximately 1/16 inch thick rigid plastic or rubber which is coated with a thin layer of heat reflective material to reflect heat from the heating source back into the fluid cushion to heat the fluid therein. In certain applications, the inner capsule portion may be factory attached and sealed at its proximal end adjacent the locking tabs, and at its distal end, by use of the stabilizer/transfer tube positioned accordingly.

In certain applications, the capsule liner is made of an approximately 1/16 inch thick rigid rubber casing, and has attached to it approximately (1/8 inch×1/8 inch) soft silicone rings/ribs formed at an inside portion to provide simulating sensation to the user during intercourse. In certain applications, the diameter of the capsule liner may be approximately 1/32 of an inch narrower than the diameter of the inner capsule portion, for instance. In certain other applications, the proximal end of the capsule liner may have a rim that is approximately 3/32 of an inch wider than that of the cross-section of its opening, and approximately 1/16 of an inch thicker than at such opening.

In certain applications, a tip portion extending from the distal end of the inner capsule portion is sealed, and in other applications is open, with respect to the stabilizer tube. In certain sample applications, the tip portion forms end tubes whose outer diameter measures approximately 3/16 of an inch, and whose length is approximately 1/4 of an inch. In certain sample applications, an inside diameter is approximately 1/8 of an inch. When sperm transfer is desired, an open-ended tip portion is used, and when sperm transfer is not desired, a closed-ended tip portion is used. Furthermore, in certain embodiments, the wearer can wear a condom inside using either configuration.

In certain applications, the stabilizer tube is made from the same material as the inner capsule portion, and is attached as a factory-attached extension thereon. In certain sample applications, this stabilizer tube is approximately 1/2 inch in length from a tip of a distal end of the inner capsule portion to the inside tip at the head of the outer capsule portion. In certain other sample applications, the stabilizer tube has an inside diameter of approximately 5/16 inch and an outside diameter of approximately 7/16 inch. In certain applications, the length of the stabilizer tube may be shortened to achieve sperm transfer.

In certain applications, the helical heating element is Teflon coated and factory attached in a spiral pattern to an outside wall of the inner capsule portion and uses heat resistant glue to pick up heat from a junction it forms with embedded heat wires. This heat is then evenly spread along the fluid cushion.

In certain applications, the opening at the base region of the prosthetic capsule has an indented circumference which is approximately 1/32 of an inch wider than that of a rim portion of the capsule liner. In certain embodiments, this rim may be stabilized with a light smear of lubricant.

In certain sample applications, the optional bend junction is located approximately 1/16 of an inch in front of an annular yoke ring structure of the retention garment to extend approximately an 1 inch therefrom.

In certain applications, a feeder valve may be used to inject air or gel into the fluid cushion. This feeder valve may be a pressure inlet which permits re-filling of the fluid cushion.

Retention Garment:

In certain exemplary applications, the retention garment may additionally hold a battery pack with heat transfer wires coupled thereto. Depending on user preference, such retention garment may be formed with either a waist-and-buttock, or a waist-and-thigh configuration for use. In certain other applications, the retention garment may include the following additional sub-components:

In certain applications, a rigid rubber O-ring type yoke holds the retention straps coupled to the pelvic base. This O-ring yoke also holds the prosthetic capsule in place. In certain applications, a ring thickness of such O-ring yoke is approximately 3/16 of an inch. The O-ring yoke may additionally be equipped with an approximately 1/8 of an inch thick soft gel ring to provide cushioning between its nylon strands and the user's partner.

In certain applications, the retention garment may include waist straps which contain a battery pocket for a battery pack, and a wiring tunnel for heat transfer wires. This waist strap may have a fixed length to be paired with the O-ring yoke. Furthermore, in certain applications, the battery pocket may be elastic to stretch and hold a battery pack that measures approximately 2 inches wide, 3 inches long, and 3/4 of an inch thick. In certain applications, this battery pocket may hold a 7 volt battery securely in place, for instance, and such pocket may be located on left and right sides of the waist strap. In certain applications, the wire tunnel provides a channel for heat transfer wires to extend from the battery to the heat wire receptacle.

In certain applications, the retention garment includes a locking strap configured to provide tight and non-slip bond between the user's body and the prosthetic capsule. This strap in certain applications includes a rigid rubber ratchet grip of suitable type known in the art that locks into a selected groove which is attached to a strong nylon belt. The locking strap may also in other applications include an open end and a grip end which form an adjustable locked loop when connected to each other.

In certain applications, a buttock strap is attached at the front to the O-ring, while both rear sides connect to form a tight loop around the wearer's buttocks. A thigh strap may also be attached in certain applications at the front of the O-ring yoke structure, while the rear of each side forms a loop around the left and right thighs. In certain exemplary uses, these straps are approximately 2 inches wide, and made of non-stretch fabric. In certain other exemplary uses, these straps are tethered at the O-ring yoke structure by approximately 1/16 inch diameter and include approximately 1/2 inch long braided nylon strands.

In certain applications, a soft gel stretch ring structure is approximately 1/16 of an inch less in inner diameter than the O-ring yoke structure, so as to be stretched to friction fit in front of the O-ring yoke, and thereby protect against skin abrasion from the nylon tether stranding.

Heat and Comfort Package:

This package adds a higher level of comfort and pleasure when utilized. In certain applications, it includes such elements as a heat receptacle safety plug which is always in place when heat transfer wires are not plugged in. When heat is not being used, this package may include safety plugs that are inserted into left and right side receptacles. Further, when heat is used, a separate plug may be inserted into the side opposite the heat transfer wires. In certain embodiments, the safety plugs may be formed as rubber gaskets that normally remain plugged into the heat wire receptacles when heat transfer wires are not plugged in. This safety plug keeps debris and moisture out of the capsule. In certain sample applications, heat transfer wires may be 12 gauge insulated wires. In these applications, the wires include a female lead at the battery end, and a male lead at the pelvic base end. One end connects to the battery on the retention garment, and the other end connects to a heat wire receptacle formed in the capsule. A lithium ion battery pack (which in certain applications may have a voltage of 7 Volts), for example, provides the heat that is transported through heat transfer wires to the helical heating element. This battery pack in certain applications has multiple heat settings such as low, medium, and high.

Conditioning Station:

In certain applications, this station is constructed of rigid plastic to allow the prosthetic capsule to dry in privacy after being cleaned. After cleaning, the prosthetic capsule may be lightly towel dried and then placed inside the conditioning station to complete the drying process. The conditioning station in certain applications includes ventilation holes to allow free flow of air which may be increased by a fan portion located, for instance, at the base of such station. The conditioning station may include the following sub-component in certain applications:

A base with screw-on legs which has a depth of approximately 3/4 of an inch and a length of approximately 3/4 of an inch. In certain applications, the leg attachments are disposed at corners at 12×12 inch spacing.

A fan units may be provided at the bottom of the base to circulate air through ventilation holes in a tower portion of the conditioning station. In certain applications, the fan unit may measure approximately 5 inches in diameter for ample fit within the station.

A power cord may be employed to draw electrical power from the wall outlet to the fan unit.

A lock loop which in certain exemplary uses measures 1/4 of an inch in diameter may be located at the top front of the conditioning station base to allow use of a lock.

The conditioning station may be formed with sides which in certain applications measure approximately 10 and 3/8 of an inch in height, not including 1/4 inch long pins engaging the base/side pin receptacles. These sides may be formed by mutually hinged sections which lock together to form a square in certain applications, with pins inserted into side grooves and base/side pin receptacles on the base. The side grooves are located in the base and top and used to align the sides. The base/side pin receptacles are located in the base and top, and in certain applications have a depth of approximately 1/8 of an inch. The bottom and top pins of the 4 Sides are inserted into the receptacles for added strength and security.

The conditioning station may include a top which in certain applications measures approximately 12 inches×12 inches, with a thickness which in certain applications measures 1/4 of an inch. In certain other applications, the top may include a latch loop on its front, and two rear locking labs on its back. The latch loop accepts the top end of a latch strap, and the rear locking tabs insert into corresponding slots at the top of the rear portion of the side.

The latch strap in certain applications is made of aluminum or other such material of suitable strength and readily portable weight. In certain other applications, a hook may be provided at a top end, and a slot at a lower end to secure the base, sides, and top to the lock loop by use of a lock.

Flange cradles which measure approximately 4 inches high, not including the 1/4 inch pins that are inserted into the base. In certain applications, they are made of rounded hard rubber with an approximately 3/16 inch diameter, each crudely being thereby approximately 7 inches high.

Device/insert holders which allow inside-outside drying of the prosthetic capsule. In certain applications, the holders measures approximately 1 inch in diameter, and 5 inches in length. In certain applications, they are made of plastic with ventilation holes.

Accessory hangers which in certain applications are formed as plastic hooks which fit into designated slots in the sides to hang cleaning brushes, soft gel rings, or other components or sub-components of the system.

Cleaning brushes which in certain applications are made of soft bristle nylon with rigid rubber stems and hanging loops to clean inside and the capsule.

Carrying Case:

In certain applications, the carrying case is designed to carry the prosthetic capsule, the retention garment, and the heat and comfort package. In certain exemplary uses, it may include zippered cases. In certain applications, these zippered cases may be made of polyester with an additional waterproof inside lining.

To Operate the Penile Prosthetic System:

If the temporary outer skin layer is being utilized, the following steps may be taken:

Remove the disposable outer skin from its packaging, unfold it, and place it on a clean cloth.

Apply lubricant along the outer capsule portion.

Stretch a retention band formed into the proximal end of the disposable outer skin, and pull down over the prosthetic capsule head and down towards a lower notch/groove formed near the capsule base. The band formed into the distal end will slide into the upper notch. Release pressure and let the band settle into the notch. If the bands do not seat firmly into the notches, use skin retainer rings to secure the bands.

If either of the temporary outer skin layer or the permanent outer skin layer is being utilized, the following steps may be taken:

Select whether an open-ended or closed-ended insert/liner will be used. Then place a small amount of lubricant around the opening of the inner capsule portion, and slide the insert into place. The insert must be aligned with the stabilizer tube. Insert the back end of the prosthetic capsule through the front of the pelvic base, and turn accordingly to lock the locking tabs.

Select the choice of two strap systems (Waist and Buttock, or Waist and Thigh). Slide the O-ring yoke of the retention garment over the prosthetic capsule head and back to the pelvic base. Match alignment marks on the O-ring yoke with those on the pelvic base.

If the heat option is being used, remove the receptacle safety plug and plug the male end of the heat transfer wire into the receptacle. The side opposite the heat transfer wire must be secured by a receptacle safety plug.

Thread the heat transfer wire through a wire tunnel.

Position the prosthetic capsule opening at the head of the penis and insert the penis into the opening and loosely fasten the waist strap around the waist. Lightly secure the other straps (Buttock or Thigh).

If using the heat option, insert the battery into the battery pocket on the waist strap, and pull the female end of heat transfer wires through the appropriate wire tunnel to be plugged into the battery. Stretch the soft gel ring and pull it over the head of the prosthetic capsule down to rest against the front of the O-ring yoke.

Maintenance of the Penile Prosthetic System:

All components should be cleaned using anti-bacterial soap and warm water. Furthermore, they should be rinsed and placed in the conditioning station to be dried. In certain embodiments, a large soft bristle brush of the conditioning station can be used to clean inside the capsule liner and the inner capsule portion. Use the smaller Brush to clean inside the hollow Stabilizer/Transfer Tube and the open ended tip of Insert. The Batteries and Wires must always be removed prior to cleaning and the safety plugs must also be in place.

Although the subject penile prosthetic system has been described in connection with specific forms and uses thereof, it will be appreciated that various modifications other than those discussed above may be resorted to without departing from the spirit or scope of the system as defined in the appended claims. For example, functionally equivalent elements may be substituted for those specifically shown and described, certain features may be used independently of other features, and in certain cases, particular locations of the elements may be reversed or interposed, all without departing from the spirit or scope of the system as defined in the appended claims.

What is claimed is:

1. A penile prosthetic system, comprising:
   a prosthetic capsule extending longitudinally from a base region to define a shaft region terminating at a tip region, said prosthetic capsule including:
      an inner capsule portion nested within an outer capsule portion and a fluid cushion captured therebetween;
      said inner capsule portion defining an inner bore extending from the base region longitudinally through the shaft region, said inner capsule portion being supported with respect to said outer capsule portion at the tip region by a stabilizing member; and,
      an outer skin layer extending substantially about at least a portion of the shaft region of said prosthetic capsule, said outer skin layer being configured to emulate penile shaft skin;
   wherein said stabilizing member projects from said inner capsule portion to matingly engage a tip passage formed through said outer capsule portion at the tip region, said stabilizing member defining a transfer tube for open communication therethrough between the inner bore of said inner capsule portion and the tip passage of said outer capsule portion.

2. The system as recited in claim 1, further comprising a heating source coupled to transfer heat to said prosthetic capsule for thermal emulation of a naturally erect penis.

3. The system as recited in claim 1, further comprising a pelvic base having a substantially planar body and a base opening formed therethrough, the base region of said prosthetic capsule detachably coupling to said pelvic base for support with the inner bore of said inner capsule portion aligned in open communication with the base opening.

4. The system as recited in claim 3, further comprising a retention garment including at least one retention strap coupled to said pelvic base for adjustable securement about a portion of a user's body.

5. The system as recited in claim 1, further comprising a capsule liner removably inserted within the inner bore of said inner capsule portion, said capsule liner defining an inner space for receiving a user's penis in substantially conformed manner;
   wherein said capsule liner is formed of a flexible material, said capsule liner having a plurality of ribs formed about an intermediate portion thereof, said capsule liner converging to a liner tip substantially aligning with said stabilizing member when fully inserted within the inner bore of said inner capsule portion.

6. The system as recited in claim 1, wherein said prosthetic capsule includes a fluid cushion sealed within a canal defined between said inner and outer capsule portions; and, a heating source is disposed on said inner capsule portion in communication with the canal to transfer heat to said fluid cushion.

7. The system as recited in claim 6, wherein said heating source includes at least one helical element configured to extend about an outer wall of said inner capsule portion substantially through the shaft region, said heating source being thermally charged responsive to actuation through a link to an external source passed through at least a portion of said prosthetic capsule.

8. The system as recited in claim 1, wherein each of said inner and outer capsule portions is formed of a resilient material, said inner capsule portion being configured with greater firmness than said outer capsule portion.

9. The system as recited in claim 1, wherein said outer skin layer includes a removable elastic tubular member releasably ensleeving said outer capsule portion substantially along the shaft region.

10. The system as recited in claim 1, further comprising a conditioning station for at least said prosthetic capsule, said conditioning station including:
   a support panel having a perforated surface extending over a blower compartment, said support panel having at least one supporting member coupled thereto for receiving at least a portion of said prosthetic capsule; and, a blower unit disposed in said blower compartment, said blower unit being actuated to generate air flow past said supporting members.

11. The system as recited in claim 1, wherein said outer skin layer includes a flexible tubular member releasably ensleeving said outer capsule portion substantially along the shaft region, said outer capsule portion at the tip region emerging from said tubular member.

12. A penile prosthetic system, comprising:
a pelvic base having a substantially planar body and a base opening formed therethrough;
a prosthetic capsule having a base region detachably coupled to said pelvic base, said prosthetic capsule extending longitudinally from the base region to define a shaft region terminating at a tip region, said prosthetic capsule including:
an inner capsule portion nested within an outer capsule portion and a fluid cushion captured therebetween;
said inner capsule portion defining an inner bore extending from the base region longitudinally through the shaft region, said inner capsule portion being supported with respect to said outer capsule portion at the tip region by a stabilizing member, said inner capsule portion being supported at the base region with the inner bore thereof aligned in open communication with the base opening of said pelvic base;
a heating source coupled to said inner capsule portion to transfer heat thereto; and,
an outer skin layer extending substantially about at least a portion of the shaft region of said prosthetic capsule, said outer skin layer being configured to emulate penile shaft skin;
wherein said heating source is controlled to responsively tune a thermally-dependent fluid property of said fluid cushion, said prosthetic capsule being thereby selectively tuned in stiffness.

13. The system as recited in claim 12, wherein said fluid cushion is sealed within a canal defined between said inner and outer capsule portions; and, said heating source is disposed on said inner capsule portion in communication with the canal to transfer heat to said fluid cushion.

14. The system as recited in claim 13, further comprising a retention garment including at least one retention strap coupled to said pelvic base for adjustable securement about a portion of a user's body.

15. The system as recited in claim 13, further comprising a capsule liner formed of a flexible material removably inserted within the inner bore of said inner capsule portion, said capsule liner defining an inner space for receiving a user's penis in substantially conformed manner, said capsule liner having a plurality of ribs formed about an intermediate portion thereof, said capsule liner converging to a liner tip substantially aligning with said stabilizing member when fully inserted within the inner bore of said inner capsule portion.

16. The system as recited in claim 13, wherein said heating source including at least one helical element configured to extend about an outer wall of said inner capsule portion substantially through the shaft region.

17. The system as recited in claim 13, wherein:
each of said inner and outer capsule portions is formed of a resilient material, said inner capsule portion being configured with greater firmness than said outer capsule portion, each of said inner and outer capsule portions being formed of at least one material selected from the group consisting of: rubber, silicone, polyurethane, and foam;
said stabilizing member projects from said inner capsule portion to matingly engage a tip passage formed through said outer capsule portion at the tip region, said stabilizing member defining a transfer tube for open communication therethrough between the inner bore of said inner capsule portion and the tip passage of said outer capsule portion; and,
said outer skin layer includes a removable elastic tubular member releasably ensleeving said outer capsule portion substantially along the shaft region.

18. The system as recited in claim 12, wherein said outer skin layer includes a flexible tubular member releasably ensleeving said outer capsule portion substantially along the shaft region, said outer capsule portion at the tip region emerging from said tubular member.

19. A penile prosthetic system having thermal regulation, comprising:
a pelvic base having a substantially planar body and a base opening formed therethrough, said pelvic base including at least one retention strap coupled to said planar body for adjustable securement about a portion of a user's body;
a prosthetic capsule having a base region detachably coupled to said pelvic base, said prosthetic capsule extending longitudinally from the base region to define a shaft region terminating at a tip region, said prosthetic capsule including an inner capsule portion nested within an outer capsule portion and a fluid cushion sealed within a canal defined therebetween, wherein:
said inner capsule portion defines an inner bore extending from the base region longitudinally through the shaft region;
said inner capsule portion is supported with respect to said outer capsule portion at the tip region by a stabilizing member projecting to matingly engage a tip passage formed through said outer capsule portion at the tip region, said stabilizing member defining a transfer tube for open communication therethrough between the inner bore of said inner capsule portion and the tip passage of said outer capsule portion;
said inner capsule portion is supported at the base region with the inner bore thereof aligned in open communication with the base opening of said pelvic base; and,
each of said inner and outer capsule portions is formed of a resilient material, said inner capsule portion being configured with greater firmness than said outer capsule portion;
at least one helical heating element integrated in said inner capsule portion configured to extend about an outer wall of said inner capsule portion substantially through the shaft region, said heating element being thermally charged responsive to actuation through a link to an external source passed through said prosthetic capsule and said pelvic base; and,
an outer skin layer extending substantially about at least a portion of the shaft region of said prosthetic capsule, said outer skin layer being configured to emulate penile shaft skin.

20. The system as recited in claim 19, further comprising a capsule liner formed of a flexible material removably inserted within the inner bore of said inner capsule portion, said capsule liner defining an inner space for receiving a user's penis in substantially conformed manner, said capsule liner having a plurality of ribs formed about an intermediate portion thereof, said capsule liner converging to a liner tip substantially aligning with said stabilizing member when fully inserted within the inner bore of said inner capsule portion.

* * * * *